United States Patent [19]

Sattler et al.

[11] 4,346,086

[45] Aug. 24, 1982

[54] CORTICOSTEROID-CONTAINING CREAM

[75] Inventors: Henning Sattler, Hamburg; Georg A. Ulex, Moorrege, both of Fed. Rep. of Germany

[73] Assignee: Beiersdorf Aktiengesellschaft, Fed. Rep. of Germany

[21] Appl. No.: 271,884

[22] Filed: Jun. 9, 1981

[51] Int. Cl.$^3$ ............................................. A61K 31/56
[52] U.S. Cl. ...................................................... 424/243
[58] Field of Search ......................................... 424/243

[56] References Cited

U.S. PATENT DOCUMENTS 3,312,590  4/1967  Elks et al. ............................ 424/243
3,924,004  12/1975  Cháng et al. ........................ 424/243
3,980,778  9/1976  Ayer et al. ........................... 424/243

OTHER PUBLICATIONS

"Merck Index" (1976) p. 536.

*Primary Examiner*—Elbert L. Roberts
*Attorney, Agent, or Firm*—Linda G. Bierman; Jordan B. Bierman

[57] ABSTRACT

A corticosteroid-containing cream comprising
(a) 0.05–0.5 parts fluocortolone
(b) 2.5–20 parts fatty acid sorbitan esters and/or a mixture of fatty acid mono- and diglycerides
(c) 1–5 parts fatty acid monoglycerides
(d) 1–10 parts beeswax
(e) 5–25 parts liquid paraffin
(f) 25–75 parts petroleum jelly and water ad 100 parts, all parts being by weight.

The cream is particularly useful as an anti-inflammatory agent for topical application.

22 Claims, No Drawings

CORTICOSTEROID-CONTAINING CREAM

Preparations containing corticosteroids intended for topical application are useful for the treatment of various skin disorders. However, in order that the active ingredients evidence their maximum effectiveness, they must be absorbed through the skin. The horny layer, the stratum corneum, forms a barrier which must be surmounted. Clearly, the therapeutic effectiveness of the corticosteroids depends greatly on the rate at which they are absorbed from the carrier base and at which they diffuse through the barrier.

One method of increasing the rate of transmission slightly is by increasing the concentration of active ingredient in the composition. However, this has important drawbacks in that there is a much greater likelihood of undesirable side effects being experienced. Therefore, it is useful to adjust the corticosteroid concentration so that the optimum therapeutic effect is achieved with a minimum concentration of active ingredient.

This has been accomplished by dissolving the corticosteroid in the base at a concentration which is close to saturation. This has been achieved by the use of such materials as glycols, low molecular weight alcohols, and solubilizers. Because of the poor solubility of the corticosteroids, up to 60% glycols must be used. In many cases, this causes skin irritations which may require cessation of the treatment. In addition, skin irritations resulting from even low concentrations of these materials have also been reported.

In view of the foregoing problems, preference must be given to a base which contains the corticosteroid in suspended form. Such bases are already known, but they contain wool fat, or derivatives thereof, and are therefore prone to exhibiting allergenic characteristics.

The effectiveness of a given corticosteroid depends on its structure and its chemical and physical properties. If the corticosteroid is contained in a base to be applied topically, the properties of the base then become important factors in determining the therapeutic effectiveness of the composition. These properties of the base depend on the type of emulsifiers and additives contained therein. It is not possible to predict, at the present time, the manner in which an emulsion system will act with a given corticosteroid. Therefore, one cannot pre select a suitable base which will permit the steroid to exhibit its maximum effectiveness.

It is among the objects of the present invention to increase the therapeutic effectiveness of the specific corticosteroid known as fluocortolone by providing a suspension base of a particular kind. As a result, a strong therapeutic action is obtained with a relatively low concentration of active ingredient. Thus, undesirable side effects are minimized.

Moreover, the new composition is at least equivalent in effect to the pre-existing compositions, despite its reduced fluocortolone content. In addition, superior skin tolerance is obtained, due to the absence of allergenic substances such as preservatives, wool fat, and glycol.

In practicing the invention, there is provided a corticosteroid-containing cream comprising 0.05–0.5 parts by weight fluocortolone
2.5–20 parts by weight fatty acid sorbitan esters and/or a mixture of fatty acid-monoglycerides and fatty acid diglycerides
1–5 parts by weight fatty acid monoglycerides
1–10 parts by weight beeswax
5–25 parts by weight liquid paraffin
25–75 parts by weight petroleum jelly and water ad 100 parts.

Another name for petroleum jelly is petrolatum.

With the foregoing composition, it is possible to obtain a water in oil emulsion which contains fluocortolone suspended in micronized form. The steroid itself, of course, is well known.

As fatty acid sorbitan esters, those with well as saturated or unsaturated medium and higher natural fatty acids, respectively paraffin monocarboxylic acids are to be preferred. Especially preferred are partial esters, or mixtures thereof, with 1 to 3 fatty acid molecules per sorbitan molecule. The fatty acids desirably have 10 to 20 carbon atoms and, in particular, contain 12 to 18 carbon atoms. Lauric and oleic acids have been found especially useful.

The sorbitan esters can be used together with a mixture of fatty acid monoglycerides and fatty acid diglycerides. It is also possible to use the sorbitan esters or the mixture of glycerides alone. Such glycerides, or mixtures thereof, can be obtained by direct esterification of one mole of glycerine with one to two moles of fatty acid. In addition, they can be obtained by partial saponification of fats. Both of these methods generally produce a mixture of mono- and diglycerides containing about 20% to about 80% by weight monoglyceride.

Preferred mixtures of fatty acid monoglycerides and fatty acid diglycerides are mixtures of esters of higher, saturated and unsaturated natural fatty acids, respectively paraffin monocarboxylic acids. These fatty acids desirably have 14 to 20 carbon atoms. Especially preferred are unsaturated fatty acids with 16 to 20 carbon atoms. Oleic acid has been found especially useful.

Furthermore the compositions of the present invention contain fatty acid monoglycerides. Preferred fatty acids are higher, saturated and unsaturated natural fatty acids, respectively paraffin monocarboxylic acids which desirably have 14 to 20 carbon atoms. Especially preferred are saturated fatty acids with 16 to 20 carbon atoms. Stearic acid has been found especially useful.

The beeswax can be white or yellow, and the paraffin can be a viscous liquid or a thin oil. The petroleum jelly is advantageously white and, in a particularly preferred form, is of pharmaceutical grade; that is, free of skin irritating components.

In producing the compositions of the present invention, the components, with the exception of the water, are thoroughly mixed with each other and heated to 75° C. The water, in a separate container, is brought to the same temperature. The two are combined with stirring, and the emulsion which forms is cooled to 30° C. It can then be placed over a roller mill.

The compositions of the invention are characterized by surprisingly high therapeutic effectiveness, due to the special composition of the suspension base. Since it contains no allergenic or skin irritating components (such as wool fat or derivatives thereof, preservatives, or alcohols, such as glycols), the unfavorable reaction problems of the prior art are not found. The properties of the present composition are particularly favorable if it is to be used under a protective dressing (under occlusion).

Under normal circumstances, inflammation or similar skin conditions which respond to anti-inflammatory agents are treated by applying a cream or ointment containing 0.05% to 0.5% fluocortolone. The application is made several times daily on the affected skin areas so that they are completely covered. Most preferably, 0.2% fluocortolone is used.

The surprising effectiveness of the compositions of the present invention, as well as the increased absorption of the fluocortolone, is demonstrated in human pharmacological tests on a substantial number of patients. The vasoconstriction tests were carried out in accordance with the procedure of McKenzie, which is generally accepted to demonstrate the inflammation-inhibiting effect of topically applied corticosteroids (A. W. McKenzie, and R. M. Atkinson: Arch. Dermatolog. 89,741 (1964)). The investigations were carried out on healthy individuals under double-blind conditions.

Test plasters having 100 mg each of the preparation to be tested were applied to the back to the right and left of the spine. The exposure time was 16 hours and the results were then evaluated after one half, two, four and eight hours. The degree of skin paling was observed and rated from 0 (no paling) to 3 (considerable paling). The degree of skin paling is a measure of the strength of the vasoconstrictive effect.

The numerical evaluation was achieved by calculating the areas under the curve obtained by plotting the average vasoconstriction values against time, as is recognized in the literature. For some ointment bases to which fluocortolone has been added, we obtained the following exemplary area values:

|   | | % by weight | |
|---|---|---|---|
| A. | fatty acid | | |
|   | mono-/-diglycerides | 1.0 | |
|   | 1,2-propylene glycol | 1.0 | area value: 10.2 |
|   | white petroleum jelly | 97.8 | |
|   | fluocortolone | 0.2 | |
| B. | fatty acid triglycerides | 45.0 | |
|   | white petroleum jelly | 54.8 | area value: 8.9 |
|   | fluocortolone | 0.2 | |
| C. | wool fat (lanolin) | 20.0 | |
|   | fatty acid triglycerides | 5.0 | |
|   | white petroleum jelly | 35.0 | area value: 11.2 |
|   | fluocortolone | 0.2 | |
|   | water | 39 8 | |
| D. | fatty acid | | |
|   | mono-/-diglycerides | 2.0 | |
|   | fatty acid esters | 5.0 | |
|   | liquid paraffin | 19.4 | |
|   | white petroleum jelly | 6.3 | area value: 11.5 |
|   | hard paraffin | 6 3 | |
|   | sorbitol | | |
|   | (70% aqueous solution) | 10.0 | |
|   | glycerin | 7.5 | |
|   | fluocortolone | 0.2 | |
|   | water | 42.3 | |

A standard ointment which contains 0.25% fluocortolone and 0.25% fluocortolone capronate yields an area value of 15.9. This value is obtained with a total of 0.5% active steroid present. The composition of the present invention, on the other hand, having a fluocortolone content of only 0.2%, yields an area value of 17 as follows:

| Cream according to the invention | | |
|---|---|---|
| | % by weight | |
| Mixture of oleic acid | | |
| mono-/-diglycerides | 10.0 | |
| stearic acid monoglyceride | 3.0 | |
| beeswax | 5.0 | area value: 17 |
| liquid paraffin | 7.0 | |

| -continued | |
|---|---|
| Cream according to the invention | |
| | % by weight |
| white petroleum jelly | 49.5 |
| fluocortolone | 0.2 |
| water | 25.3 |

The foregoing indicates clearly the greatly improved effectiveness of the composition according to the present invention. The new base increases the penetration of the active fluocortolone as compared to known preparations containing this same material. This increased effectiveness, despite the lower fluocortolone content, is particularly surprising, since increases in the area values are very difficult to achieve in the upper range.

The following examples are intended to illustrate the present invention:

EXAMPLE 1

For the production of a highly effective cream, the following components are mixed together and heated to 75° C. (All parts are by weight).

0.2 parts fluocortolone
5 parts oleic acid sorbitan ester
3 parts stearic acid monoglyceride
3 parts beeswax
14 parts liquid paraffin
48.5 parts white petroleum jelly
26.3 parts of water are heated separately to the same temperature (75° C.). Subsequently, the two phases are combined with each other under intensive stirring. An emulsion is formed which is allowed to cool to 30° C. This cream is subsequently placed over a roller mill.

EXAMPLES 2 and 3

In the same manner as described in Example 1, effective creams are obtained from the following components. (All parts are by weight):

EXAMPLE 2

0.1 parts fluocortolone
2.5 parts a mixture of oleic acid mono- and diglycerides
5.0 parts oleic acid sorbitan ester
2.0 parts stearic acid monoglyceride
5.0 parts beeswax
17.5 parts liquid paraffin
27.5 parts white petroleum jelly
40.4 parts water

EXAMPLE 3

0.4 parts fluocortolone
8.4 parts lauric acid sorbitan ester
1.0 parts stearic acid monoglyceride
2.5 parts beeswax
6.0 parts liquid paraffin
24.0 parts white petroleum jelly
57.7 parts water.

While only a limited number of specific embodiments of the present invention have been expressly described, it is, nonetheless, to be broadly construed and not to be limited except by the character of the claims appended hereto.

What we claim is:

1. A corticosteroid-containing cream comprising
(a) 0.05–0.5 parts fluocortolone (b) 2.5-20 parts fatty acid sorbitan esters and/or mixtures of fatty acid mono- and diglycerides
(c) 1-5 parts fatty acid monoglycerides
(d) 1-10 parts beeswax
(e) 5-25 parts liquid paraffin
(f) 25-75 parts petroleum jelly and water ad 100 parts, all parts being by weight.

2. A cream according to claim 1 wherein said (b) is sorbitan esters.

3. A cream according to claim 2 wherein said esters are with saturated or unsaturated medium or higher fatty acids, respectively paraffin monocarboxylic acids.

4. A cream according to claim 2 wherein there are 1 to 3 fatty acid molecules per sorbitan molecule.

5. A cream according to claim 3 wherein said fatty acids have 10 to 20 carbon atoms.

6. A cream according to claim 5 wherein said fatty acids have 12 to 18 carbon atoms.

7. A cream according to claim 6 wherein said fatty acids are lauric acid or oleic acid.

8. A cream according to claim 1 wherein said fatty acids are natural.

9. A cream according to claim 1 wherein the fatty acid of said (c) is stearic acid.

10. A cream according to claim 1 wherein said jelly is pharmaceutical grade.

11. A method of preparation of the cream of claim 1 comprising emulsifying said (a), (b), (c), (d), (e), and said petroleum jelly with said water.

12. A method according to claim 11 comprising mixing said (a), (b), (c), (d), (e), and said petroleum jelly together to form a blend, heating said blend to about 75° C., heating said water separately from said blend to about 75° C., combining said blend and said water with stirring to form an emulsion, cooling said emulsion to about 30° C.

13. A cream according to claim 1 wherein said (b) is mixtures of fatty acid mono- und diglycerides.

14. A cream according to claim 13 wherein said glycerides are with higher, saturated or unsaturated fatty acids.

15. A cream according to claim 14 wherein said fatty acids have 14 to 20 carbon atoms.

16. A cream according to claim 15 wherein said fatty acids are unsaturated fatty acids.

17. A cream according to claim 16 wherein said fatty acids have 16 to 20 carbon atoms.

18. A cream according to claim 17 wherein said fatty acid is oleic acid.

19. A cream according to claim 1 wherein said monoglycerides of said (c) are with higher, saturated and unsaturated fatty acids.

20. A cream according to claim 19 wherein said fatty acids have 14 to 20 carbon atoms.

21. A cream according to claim 20 wherein said fatty acids are saturated fatty acids.

22. A cream according to claim 21 wherein said fatty acids have 16 to 20 carbon atoms.

* * * * *